US012125204B2

(12) United States Patent
Bradley (10) Patent No.: US 12,125,204 B2
(45) Date of Patent: Oct. 22, 2024

(54) RADIOGENOMICS FOR CANCER SUBTYPE FEATURE VISUALIZATION

(71) Applicant: Infotech Soft, Inc., Miami, FL (US)

(72) Inventor: Ray Mathew Bradley, Miami, FL (US)

(73) Assignee: Infotech Soft, Inc., Miami, FL (US)

( * ) Notice: Subject to any disclaimer, the term of this patent is extended or adjusted under 35 U.S.C. 154(b) by 405 days.

(21) Appl. No.: 17/836,555

(22) Filed: Jun. 9, 2022

(65) Prior Publication Data

US 2023/0401697 A1  Dec. 14, 2023

(51) Int. Cl.
| | |
|---|---|
| G06K 9/00 | (2022.01) |
| A61K 35/12 | (2015.01) |
| G06T 7/00 | (2017.01) |
| G06V 10/46 | (2022.01) |
| G06V 10/762 | (2022.01) |
| G06V 10/77 | (2022.01) |
| G06V 10/774 | (2022.01) |
| G06V 10/778 | (2022.01) |
| G06V 10/80 | (2022.01) |
| G06V 10/82 | (2022.01) |
| G06V 20/20 | (2022.01) |
| G16H 30/40 | (2018.01) |
| G16H 50/70 | (2018.01) |
| G16H 70/60 | (2018.01) |

(52) U.S. Cl.
CPC .......... *G06T 7/0012* (2013.01); *G06V 10/462* (2022.01); *G06V 10/762* (2022.01); *G06V 10/7715* (2022.01); *G06V 10/7747* (2022.01); *G06V 10/778* (2022.01); *G06V 10/811* (2022.01); *G06V 10/82* (2022.01); *G06V 20/20* (2022.01); *G16H 30/40* (2018.01); *G16H 50/70* (2018.01); *G16H 70/60* (2018.01); *G06T 2207/30096* (2013.01)

(58) Field of Classification Search
CPC ............. A61K 35/12; G06K 9/00; G06T 7/00
USPC ....... 382/100, 103, 128–134, 156, 162, 168, 382/173, 181, 214, 219, 224, 254, 274, 382/276, 286–291, 305, 312; 378/4, 21
See application file for complete search history.

(56) References Cited

U.S. PATENT DOCUMENTS

| | | | | |
|---|---|---|---|---|
| 9,996,664 | B2 * | 6/2018 | Lloyd | H04L 67/12 |
| 11,324,469 | B2 * | 5/2022 | Jacobs | G06F 18/40 |
| 11,348,661 | B2 * | 5/2022 | Yip | G06N 3/045 |
| 11,935,152 | B2 * | 3/2024 | Yip | G06T 7/0012 |
| 2016/0242690 | A1 * | 8/2016 | Principe | A61B 5/316 |
| 2021/0090694 | A1 * | 3/2021 | Colley | G16H 15/00 |

(Continued)

*Primary Examiner* — Seyed H Azarian
(74) *Attorney, Agent, or Firm* — Mark Terry (57) ABSTRACT

A computer implemented method and system for identifying and visualizing features correlated with cancer subtypes, includes the steps of receiving a set of medical images representing an area including a patient's lesion, applying a classification model trained on lesions with known pathology by mathematically combining the model's learned weights with said medical images to produce a score indicating the likelihood of the lesion being of each particular cancer subtype, extracting importance maps from said classification model indicating features correlated with each cancer subtype by tracing the output of the model through the learned weights to identify regions of the input with a strong influence on the classification score for each cancer subtype, and displaying said importance maps visually on a computing device.

16 Claims, 4 Drawing Sheets

(56) References Cited

U.S. PATENT DOCUMENTS

2021/0248736 A1\* 8/2021 Kamen ................ G06F 18/214
2021/0407674 A1\* 12/2021 Winkel .................... G06N 3/08

\* cited by examiner

RADIOGENOMICS FOR CANCER SUBTYPE FEATURE VISUALIZATION

STATEMENT REGARDING FEDERALLY SPONSORED RESEARCH OR DEVELOPMENT

The invention was made with government support under contract 75N91021C00025 awarded by the National Institutes of Health. The government has certain rights in the invention.

CROSS-REFERENCE TO RELATED APPLICATIONS

Not Applicable.

INCORPORATION BY REFERENCE OF MATERIAL SUBMITTED ON A COMPACT DISC

Not Applicable.

TECHNICAL FIELD

The claimed subject matter relates to the field of computer aided phenotyping of cancerous lesions from medical images. More particularly, the claimed subject matter relates to computer implemented methods for processing medical images and highlighting portions of an image correlated to specific cancer subtypes.

BACKGROUND

Cancer is a biologically diverse disease, showing differences in molecular alterations, cellular composition, and clinical outcome. Through gene expression profiling and other techniques various cancer subtypes have been identified and shown to have critical differences in occurrence, survival, and treatment responses. The use of knowledge about underlying subtypes driving the patient's tumor to guide treatment strategies is referred to as precision medicine. This requires the identification of an individual patient's subtypes, generally based on genomic information derived from a tumor specimen obtained through a biopsy. However, tumors exhibit a large amount of heterogeneity both within a single lesion and across different lesions within a patient. Tumor heterogeneity manifests itself in tumor morphology, biomarker expression, genetic mutations, and histopathologic characteristics. The high level of intra-tumoral variation makes biopsies subject to sampling errors leading to samples that may not be representative of the genetic, epigenetic, or phenotypic alterations of an entire tumor, yet sectioning of an entire tumor for analysis is not practical. Furthermore, tumors constantly evolve, modifying their genomic and phenotypic composition, especially under the selection pressure of therapeutic intervention, forcing oncologists to chase a constantly changing disease. While immunohistochemistry (IHC) surrogates are a common alternative to full genetic characterization, which may be costly, they have been shown to be suboptimal with variable agreement with formal genetic testing. In addition, such surrogates have not been identified for many genetic defects. These issues may lead to both under-diagnosis of lethal cancers and over-treatment of indolent cancers.

Radiology imaging in cancer has been at the forefront of reducing mortality, with early and routine magnetic resonance imaging (MRI) or computed tomography (CT) screening for high-risk individuals becoming more common. Medical imaging allows for the non-invasive, fast, and low-cost acquisition of radiomic biomarkers to longitudinally characterize the radiographic phenotype of a tumor such as molecular subtype and intratumor heterogeneity, allowing tumor staging and prognosis at a level that truly achieves the concept of precision medicine. Recent studies have shown that a multiparametric MRI (mpMRI) approach provides improved diagnostic performance for breast cancer than individual methods by interrogating multifaceted tumor biology. Dynamic Contrast-Enhanced (DCE) MRI sequences can detect the increased vascularity frequently occurring in tumors due to abnormal angiogenesis to provide insights into tumor biology and have demonstrated the ability to differentiate radiation necrosis from tumor progression. Diffusion weighted MRI (DWI) probes the free diffusivity of water molecules to assess cellularity and cell membrane integrity. The restriction of diffusion is quantitatively analyzed based on the apparent diffusion coefficient (ADC) that describes signal attenuation with increasing b-values. DWI has proven to increase the accuracy of breast cancer detection versus DCE-MRI alone and can be used to distinguish between benign and malignant lesions, stratify in-situ from invasive disease, and potentially predict response to treatment over time.

Radiomics refers to the high-throughput extraction of quantitative features from the vast amounts of standard of care imaging data that may correlate with the underlying biology or clinical outcomes. The extraction of quantitative features may be performed using handcrafted features or formulas based on intensity histograms, shape attributes and/or texture; or may be learned through the application of complex deep learning models. Radiogenomics searches for relationships between the quantitative imaging features representing phenotypical tumor characteristics and the genomic profile of the cancer biopsy. Tumor imaging provides non-invasive measures for capturing the phenotypical traits that may be linked to underlying genomic characteristics.

Convolutional neural networks (CNNs) are a type of artificial neural network commonly applied in computer vision tasks. Their design was inspired by the structure of neurons within the visual cortex, where individual neurons only respond to stimuli in a restricted overlapping regions of the visual field, referred to as the receptive field. This structure enables the CNN to learn filters able to discern the presence of a feature within the receptive fields of an image. A CNN is made up of three main types of layers: convolutional, pooling, and fully-connected. The convolutional layer takes input data and sweeps the filter across the image calculating the dot product at each position generating a feature map, which acts as input to the following layer. Multiple convolutional layers may be used, where subsequent layers are able to detect higher level features within the input data. Pooling layers conduct dimensionality reduction for feature maps to introduce translation invariance to small distortions and decrease the number of learnable parameters. Fully-connected layers are used at the end of the network to map the learned input features to the final output for the network, such as the probabilities for each class in the classification task. A drawback to deep learning architectures such as CNNs is their lack of interpretability. In precision medicine, where clinicians need more information to support diagnosis and treatment decisions beyond a model's decision, explanations of the model's outputs are critical to better understand a patient's unique disease state. Allowing radiologists to inspect class discriminative visualizations highlighting image regions used in inferences, such as tumor subtype classification, can help users establish trust in the model and gain greater insight into image features correlated with the model's outputs. Explanation approaches may be grouped into three basic categories: visualization, distillation, and intrinsic. Visualization approaches apply scientific visualization to highlight input characteristics that strongly influence a model output. Model distillation approaches use a separately developed white-box model trained to mimic the behavior of the model to be explained and identify the decision rules or input features influencing the model's outputs. Intrinsic methods refer to models that were designed specifically to render an explanation along with the model's output.

Therefore, what is needed is a system and method for improving the problems with the prior art, and more particularly for a more expedient and efficient method and system for facilitating the identification of specific cancer subtypes in medical images.

BRIEF SUMMARY

In one embodiment, a computer implemented method and system for identifying and visualizing features correlated with cancer subtypes, includes the steps of receiving a set of medical images representing an area including a patient's lesion, applying a classification model trained on lesions with known pathology by mathematically combining the model's learned weights with said medical images to produce a score indicating the likelihood of the lesion being of each particular cancer subtype, extracting importance maps from said classification model indicating features correlated with each cancer subtype by tracing the output of the model through the learned weights to identify regions of the input with a strong influence on the classification score for each cancer subtype, and displaying said importance maps visually on a computing device.

Additional aspects of the claimed subject matter will be set forth in part in the description which follows, and in part will be obvious from the description, or may be learned by practice of the claimed subject matter. The aspects of the claimed subject matter will be realized and attained by means of the elements and combinations particularly pointed out in the appended claims. It is to be understood that both the foregoing general description and the following detailed description are exemplary and explanatory only and are not restrictive of the disclosed subject matter, as claimed.

BRIEF DESCRIPTION OF THE SEVERAL VIEWS OF THE DRAWINGS

The accompanying drawings, which are incorporated in and constitute part of this specification, illustrate embodiments of the claimed subject matter and together with the description, serve to explain the principles of the claimed subject matter. The embodiments illustrated herein are presently preferred, it being understood, however, that the claimed subject matter is not limited to the precise arrangements and instrumentalities shown, wherein:

DETAILED DESCRIPTION

The following description includes many specific details for the purpose of illustration only and should not be understood to limit the claimed subject matter. Moreover, certain features which are well known in the art are not described in detail to avoid complication of the claimed subject matter. In addition, it will be understood that features in one embodiment may be combined with features in other claimed embodiments.

In accordance with one embodiment, computer implemented methods and systems are provided for detecting and displaying imaging features correlated with specific cancer subtypes. The specific classes of cancer subtypes may be based on current clinical or biomedical knowledge, the presence or lack of specific proteins determined using IHC assays, based on differential gene expression within tumors, or discovered through clustering of patient case data. In accordance with some embodiments, in response to receiving a set of patient images capturing part of their anatomy containing a suspicious lesion the system applies a classification model trained on tumors with known pathology to determine possible subtypes of the patient's specific lesion. After inference, the system extracts importance values from the classification model for specific image sections related to each subtype for the particular type of cancer. The importance values are combined into an importance map for each input image. Where the importance values making up the importance map are directly correlated with the importance given to each feature in the overall subtype prediction. The importance maps are transformed into visual presentations highlighting image features correlated with the specific cancer subtypes and may be presented on a computing device.

There has thus been outlined, rather broadly, the more important features of the claimed embodiments in order that the detailed description thereof that follows may be better understood, and in order that the present contribution to the art may be better appreciated. There are, of course, additional features of the claimed embodiments that will be described hereinafter and which will form the subject matter of the claims appended hereto.

In this respect, before explaining at least one embodiment in detail, it is to be understood that the claimed embodiments are not limited in its application to the details of construction and to the arrangements of the components set forth in the following description or illustrated in the drawings. The claimed embodiments are capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods, and systems for carrying out the purposes of the claimed embodiments. It is important, therefore, that the claims be regarded as including such equivalent constructions insofar as they do not depart from the spirit and scope of the claimed embodiments.

These together with other objects of the claimed embodiments, along with the various features of novelty which characterize the claimed embodiments, are pointed out with particularity in the claims annexed to and forming a part of this disclosure. For a better understanding of the claimed embodiments, its operating advantages and the specific objects attained by its uses, reference should be had to the accompanying drawings and descriptive matter in which there is illustrated preferred claimed embodiments.

The claimed embodiments involve the processing of medical images of a patient's lesion using a classification model trained on patients of known pathology to identify and visualize features correlated with specific cancer subtypes. Medical imaging is the technique and processes for capturing a visual representation of the interior of a patient's body for clinical analysis and possible medical intervention. Medical images produced through medical imaging seeks to reveal internal structure hidden by the skin and bones, which may be compared to databases of normal anatomy and physiology to identify possible abnormalities. Medical image acquisition devices that are used to capture medical images, may include any such device in common use for any specific type of cancer. This may include one or more of magnetic resonance imaging (MRI), computed tomography (CT), positron emission tomography (PET), ultrasound, x-ray, or mammogram. When using multi-parametric imaging, which refers to the performance of a sequence of medical imaging procedures that follow a specific protocol, a single image acquisition device may create multiple image sequences to be processed. Once captured medical images may be stored using one of the many medical image formats in current use, such as Digital Imaging and Communications in Medicine (DICOM), Neuroimaging Informatics Technology Initiative (NIFTI), Medical Imaging Net CDF (MING), MetaImage, or Analyze. The DICOM standard constitutes the backbone of todays medical imaging department. It defines not only a file format for storing medical images, but also a network communication protocol for their transfer, and is supported by all major medical imaging devices. Furthermore, medical images may be represented in any of the non-medical specific image formats in common use such as JPEG, PNG, TIFF, etc.

A lesion is any damage or abnormal change in the tissue of an organism that may have been caused through trauma or disease. Lesions formed through the abnormal and excessive growth of tissue uncoordinated with surrounding tissue are referred to as neoplasms. Neoplasms may be classified into four main groups: benign, in-situ, malignant, and neoplasms of uncertain or unknown behavior. Malignant lesions are commonly called cancer, if the abnormal growth forms a solid mass lesion it may be called a tumor. Cancer types are primarily defined by the organ in which they occur. Cancer subtype refers to the smaller groups that a type of cancer may be divided into based on characteristics of the cancer cells. The characteristics that define subtypes may include how the cells appear underneath a microscope, the presence of certain substances either in or on the cells, or specific mutations occurring within the DNA of the cells. The specific classes of cancer subtypes may be based on current clinical or biomedical knowledge, the presence or lack of specific proteins determined using IHC assays, based on differential gene expression within tumors, or discovered through clustering of patient case data. The value of determining the subtype of cancers is in its ability to stratify patients for more effective treatment planning and improved determination of prognosis. Pathology is the study of the causes and effects of disease or injury and addresses components of disease including cause, mechanisms of development, structural alterations of cells, and the consequences of changes. A patient of known pathology is one in which the components of their disease have been characterized by clinical staff through examination of the patient and analysis of tissue, cell, and/or body fluid samples.

In the field of artificial intelligence, a classification model is a probabilistic model that specifies the conditional probability distributions of a set of output variables given a set of input variables, allowing it to separate the inputs into a set of categories. Common classification models include logistic regression, decision tree, random forest, multilayer perceptron, convolutional neural network, and naïve bayes. Classification is a supervised learning approach where the model learns from data with known target classes to classify new unseen data. When given an input the classification model produces a classification score for each target class, which is a numerical value that is correlated with the probability the input belongs to the particular class according to the model. Training refers to the process of feeding the model inputs of known classes, comparing the classification scores of the model to the known true classes and calculating an error score, then finally updating the internal weights of the model to reduce the error score for said inputs. A trained model is one that has gone through the training process until achieving adequate performance on an unseen set of test inputs, the updated internal weights of the trained model are referred to as the model's learned weights. Performance of the model may be measured using one of many possible metrics including accuracy, precision, recall, or area under the curve (AUC).

Features refer to parts or patterns of an object in an image that help to identify the class to which it belongs. Traditional image features include properties such as corners, edges, region of interest points, ridges, etc. In the context of cancer imaging features may include microcalcifications, lesion margins, vascularity, background parenchymal enhancement (BPE), etc. Importance maps are used to associate the features that are most relevant to a specific classification. The importance map is a multi-dimensional array of float values, where each value in the map relates to a specific region of the medical image. The larger the importance value for a particular region of the image the more weight was placed on the features contained therewithin. For instance, the importance map for an image of a breast cancer lesion of the basal subtype will have larger importance values assigned to regions of the image containing smooth lesion margin and rim enhancement image features prevalent within the basal-like subtype.

Figure 1:
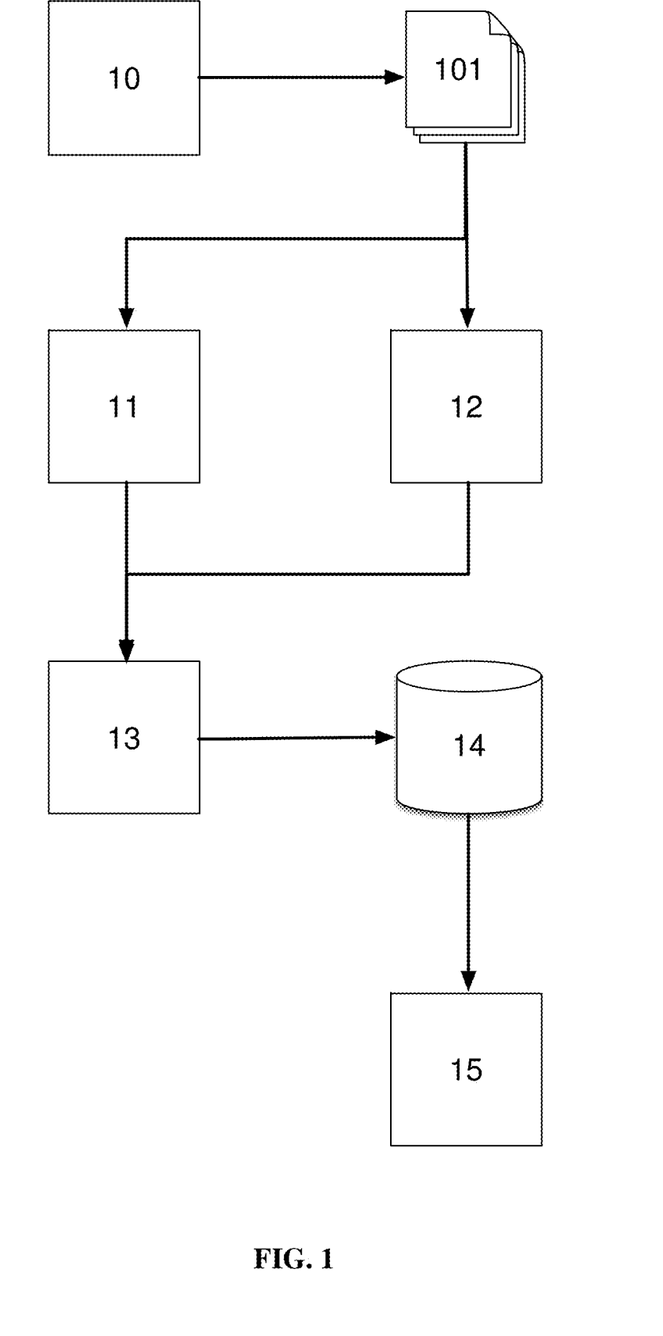
FIG. 1 provides a simplified illustration of the process for capturing medical images, calculating importance maps for the images associated to each subtype of the specific type of cancer, and retrieving the produced importance maps using standard imaging software for inspection by clinical staff.

FIG. 1 is an illustration of an exemplary system for carrying out the technologies of the claimed embodiments described herein. As shown, an image acquisition device 10, such as a magnetic resonance imaging (MRI) machine, is used to capture one or more image sequences 101 of the patient's anatomy. The image sequences can be subsequently stored locally within a computer 11 and/or remotely within a server 12. The images are then processed by the image processing component 13 either locally or within a cloud-based or software-as-a-service system external to computer 11 or server 12. Importance maps generated by 13 encode per feature numeric values correlated with the features importance for each subtype prediction and may be stored alongside the original image sequences or in other external systems 14. Finally, the images and subtype specific importance maps may be retrieved by computer 15, which may be a standard imaging workstation extended via plugin or other method, or custom image viewing software accessed locally or through a browser. The retrieved patient images are then presented to members of the oncology care team to inspect while selecting one or more importance maps to be overlayed on the image to highlight the image features correlated with possible cancer subtypes.

Figure 2:
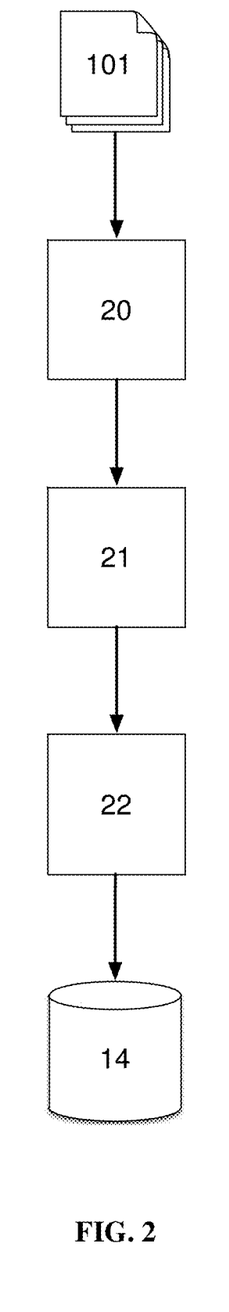
FIG. 2 provides an illustration of a possible embodiment for a processor capable of producing importance maps from captured medical images.

FIG. 2 illustrates one possible embodiment of 13. The image pre-processor 20 prepares the images 101 for input into trained classifier 21. In certain embodiments, additional inputs of radiomic image features and/or clinical, pathology, radiology, and genomic information may be provided as input to 21. 21 calculates scores for each possible subtype of the patient's cancer type. The importance map extractor 22 inspects classifier state post inference to construct importance maps conditioned on each of the subtype scores to be used to visualize important features for the subtype corresponding to the score conditioned on. The constructed importance maps may then be stored within an external storage system 14. 21 may implement multi-class classification, multi-label classification, one-vs-rest classification, one-vs-one classification, or any combination thereof to support extraction of importance maps for all possible subtypes.

An exemplative implementation of 20 may perform one or more pre-processing steps, such as the following:

Bias field correction and instrument-specific corrective procedures to reduce image anomalies introduced by the imaging equipment.

Resampling to standardize the pixel size (1-mm$^2$), voxel size (1-mm$^3$), or projection plane (axial, sagittal, coronal.)

Co-registration across images and volumes from the same study to place images within the same coordinate space and correct for patient or equipment motion between image sequences.

Organ segmentation uses organ-specific algorithms to identify and mask organs of interest. For example, breast segmentation is utilized to remove the muscle and abdominal structures to isolate breast structures, brain segmentation is utilized to remove the skull.

Anisotropic diffusion and histogram matching to reduce background noise and match signal intensities across images in a series.

Lesion segmentation to identify and isolate structures within the organ corresponding to suspected lesions or tumors.

Derived Image Generation to condense multiple image sequences into a single sequence, encoding temporal and spatial information into a multi-dimensional input; such as a subtraction of pre-contrast and post-contrast images, maximum intensity projection (MIP) images, or formulation of apparent diffusion coefficient (ADC) maps.

Radiomic feature extraction to calculate additional quantitative image features to be included as input to 21.

Region of interest identification to identify and crop a specific region of the image containing the lesion to be analyzed.

Within specific embodiments 21 may be implemented as a CNN, which may be derived from common CNN architectures, such as EfficientNet, ResNet, AlexNet, or Inception. To help alleviate the need for vast amounts of training data a transfer learning with fine-tuning approach may be used, where the model is first trained on a large generic imaging dataset, ImageNet for instance, before being fine-tuned on lesions with a known subtype. The CNN model stems are used to extract feature maps for input into shallow classification models. Feature vectors are extracted from intermediate convolutional layers within the CNN models before being pooled and concatenated into final vectors, rather than only using vectors from the final convolutional layers. Using intermediate layers captures different levels of spatial visual patterns. The extracted feature vectors are combined across image sequences to create feature vectors encompassing all available information for each patient lesion to be input into shallow classification models. The classification models perform multi-label classification to identify heterogeneous tumors with regions that exhibit features of differing subtype classes. Focal Loss is used for optimization since it down-weighs easily classified samples and focuses the loss value on more difficult samples. This loss works especially well on imbalanced data sets such as diagnosing the more rare subtype classes in cancer. Training the model 21 uses data augmentation in preprocessing layers to support GPU-accelerated augmentation during training. The classification models are evaluated using cross validation for choosing the optimal model design and hyperparameters. Once trained, the learned weights of the CNN feature maps are convolved over input images, combined by the pooling layers, and finally passed through the fully connected layers that multiply the incoming feature maps with their trained weights to produce a score of each class representing the probability said input belongs to said class.

An exemplary embodiment of 22 may utilize Gradient-weighted Class Activation Mapping (Grad-CAM), a generalization of Class Activation Mapping (CAM) a class-discriminative localization technique that generates visual explanations for CNN-based networks without the need for architectural changes or re-training. It uses gradient information flowing into convolutional layers to assign importance values to each neuron for a particular decision of interest. A separate importance map is produced for each label of the multi-class subtype classifier 21. The Grad-CAM importance map is created by first global-average-pooling the gradients of the class of interest with respect to the feature map activations of the convolutional layer of interest. The importance score a for class c and feature map k is calculated as follows:

$$\alpha_{k,c} = \frac{1}{m \cdot n} \sum_{i=1}^{m} \sum_{j=1}^{n} \frac{\partial y_c}{\partial A_{k,i,j}}$$

where $A_{k,i,j}$ is the neuron in (m×n) feature map $A_k$ at position (i,j); and $y_c$ is the logit of class c. The calculated scores represent a partial linearization of the network downstream of the CNN layer and captures the importance of the feature map to the target class. To produce the final importance map the importance scores of each feature map is linearly combined and ReLU activation is applied to only include features with a positive influence on the class of interest.

$$\text{map}_c = ReLU\left(\sum_{k}^{K} \alpha_{k,c} A_k\right)$$

This produces a course importance map the same size as the feature maps, which is up sampled to match the input image size so it may be displayed visually as an overlay on the input image. The produced importance maps may be stored without conversion, converted to multiple 2D images (such as PNG, JPEG, etc.)—with or without the underlying imaging data, converted to 3D volumes (such as NIfTI, Analyze, MetaImage, etc.), or converted to a standard format such as a DICOM series that may then be stored as a derived image within the patients record.

Figure 3:
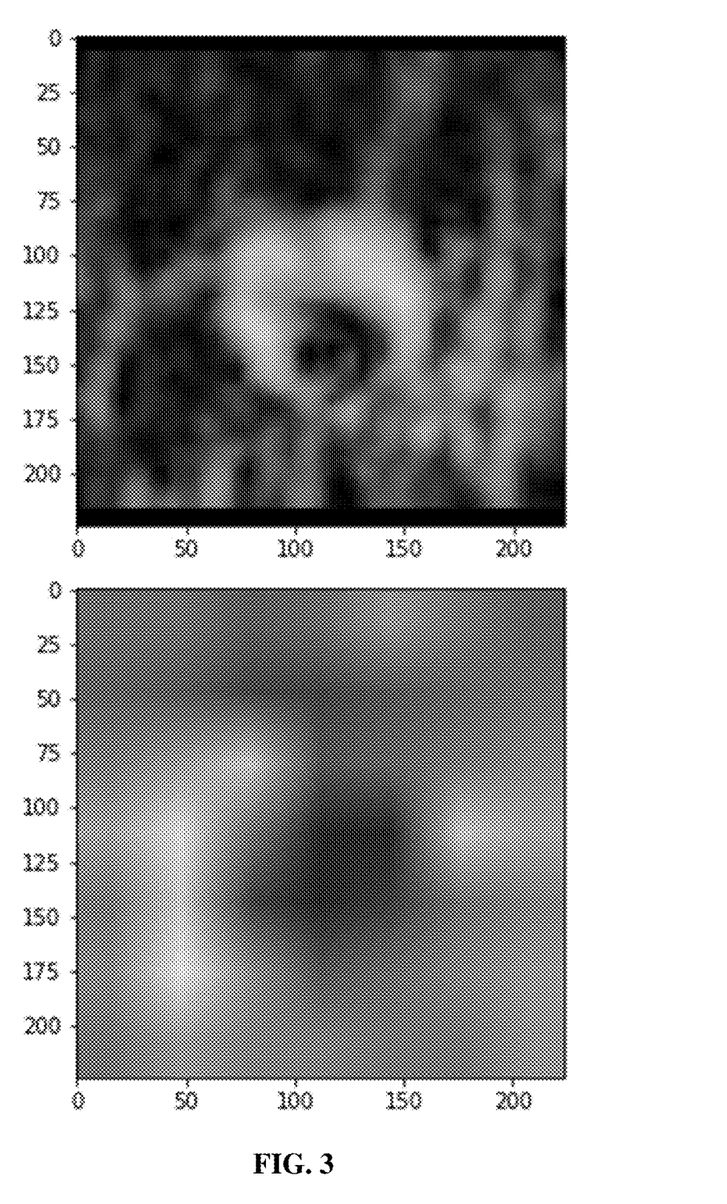
FIG. 3 provides an example medical image of a breast cancer lesion and the importance map representing regions of the image containing features correlated with the ER+ breast cancer subtype.

In an exemplary embodiment the extracted importance maps may be retrieved by clinical staff using special built plugins within their standard radiological reading station software. Through the plugin the staff may choose importance maps related to each of the cancer subtypes and overlay them on source images of the tumor, such as the T2 weighted TSE sequence or T1 weighted 3D gradient echo sequence. If multi-parametric MRIs (mpMRIs) are performed, such as dynamic contrast enhanced (DCE) or diffusion weighted imaging (DWI) sequences, the importance overlays may also be used with images derived from the various mpMRI series, for instance the maximum intensity projection (MIP) or pre and post contrast subtraction images for DCE and the apparent diffusion coefficient (ADC) map for DWI. FIG. 3 shows a post-contrast T1 image from a DCE series capturing a breast lesion and an importance map produced for estrogen receptor positive (ER+) status, where white areas highlighting the margins of the tumor indicate the regions important to the ER+ classification. By focusing on regions highlighted by the importance map the medical image reviewer can verify morphological tumor features associated with ER status. Furthermore, by comparing the importance maps for both ER+ and ER− statuses the reviewer can inspect possible heterogeneity of the underlying tumor. Based on the guidance provided by the importance map overlays the medical image reviewer can quickly confirm the radiological findings and recognize image features that are correlated with specific molecular subtypes, providing insight on the molecular makeup and possible heterogeneity of the tumor prior to a biopsy.

It is understood herein that the detailed description may be presented in terms of program procedures executed on a computer or network of computers. These procedural descriptions and representations are the means used by those skilled in the art to convey the substance of their work most effectively to other skilled in the art.

A procedure is here, and generally, conceived to be a self-consistent sequence of steps leading to a desired result. These steps are those requiring physical manipulation of physical quantities. Usually, though not necessarily, these quantities take the form of electrical or magnetic signals capable of being stored, transferred, combined, compared, and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to these quantities.

Further, the manipulations performed are often referred to in terms, such as adding or comparing, which are commonly associated with mental operations performed by a human operator. No such capability of a human operator is necessary in any of the operations described herein which form part of the claimed embodiments; the operations are machine operations. Useful machines for performing the operation of the claimed embodiments include general purpose digital computers or similar devices.

The claimed embodiments also relate to an apparatus (such as device 400) for performing these operations. This apparatus may be specially constructed for the required purpose, or it may comprise a general purpose computer as selectively activated or reconfigured by a computer program stored in the computer. The procedures presented herein are not inherently related to a particular computer or other apparatus. Various general-purpose machines may be used with programs written in accordance with the teachings herein, or it may prove more convenient to construct more specialized apparatus to perform the required method steps. The required structure for a variety of these machines will appear from the description given.

The system according to the claimed embodiments may include a general-purpose computer 400, or a specially programmed special purpose computer. The user may interact with the system via e.g., a personal computer or over a smartphone, the Internet, an intranet, etc. Either of these may be implemented as a distributed computer system rather than a single computer. Moreover, the processing could be controlled by a software program on one or more computer systems or processors or could even be partially or wholly implemented in hardware.

Portions of the system may be provided in any appropriate electronic format, including, for example, provided over a communication line as electronic signals, provided on CD and/or DVD, provided on optical disk memory, etc.

Any presently available or future developed computer software language and/or hardware components can be employed in such claimed embodiments. For example, at least some of the functionality mentioned above could be implemented using Visual Basic, C++, or any assembly language appropriate in view of the processor being used. It could also be written in an object-oriented and/or interpretive environment such as Java and transported to multiple destinations to various users.

Figure 4:
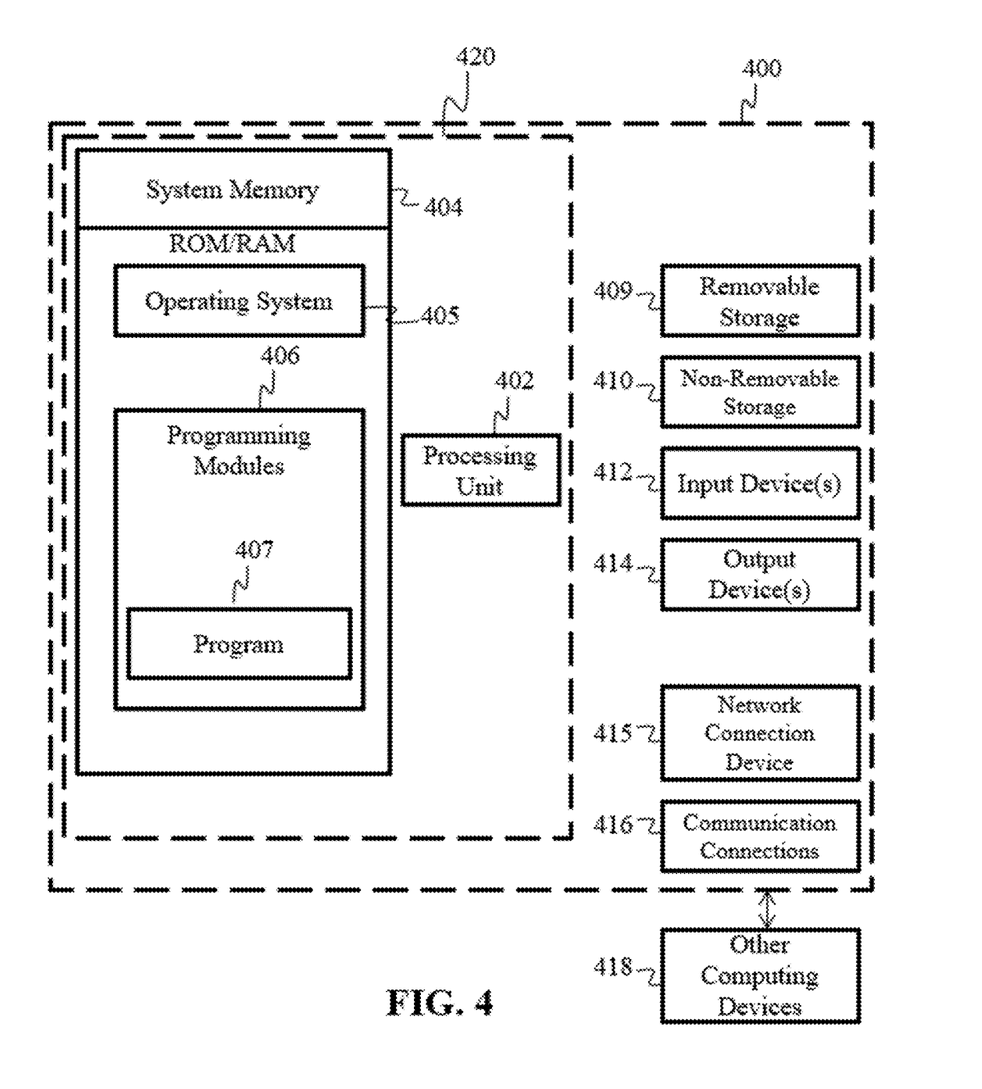
FIG. 4 is a block diagram of a system including an example computing device and other computing devices.

FIG. 4 is a block diagram of a system including an example computing device 400 and other computing devices. Consistent with the embodiments described herein, the aforementioned actions described herein may be implemented in a computing device, such as the computing device 400 of FIG. 4. Any suitable combination of hardware, software, or firmware may be used to implement the computing device 400. The aforementioned system, device, and processors are examples and other systems, devices, and processors may comprise the aforementioned computing device. Furthermore, computing device 400 may comprise an operating environment for the claimed system and method, as described above. The claimed method may operate in other environments and are not limited to computing device 400.

With reference to FIG. 4, a system consistent with an embodiment may include a plurality of computing devices, such as computing device 400. In a basic configuration, computing device 400 may include at least one processing unit 402 and a system memory 404. Depending on the configuration and type of computing device, system memory 404 may comprise, but is not limited to, volatile (e.g. random-access memory (RAM)), non-volatile (e.g. read-only memory (ROM)), flash memory, or any combination or memory. System memory 404 may include operating system 405, and one or more programming modules 406. Operating system 405, for example, may be suitable for controlling computing device 400's operation. In one embodiment, programming modules 406 may include, for example, a program module 407 for executing the actions or method steps described herein. Furthermore, embodiments may be practiced in conjunction with a graphics library, other operating systems, or any other application program and is not limited to any particular application or system. This basic configuration is illustrated in FIG. 4 by those components within a dashed line 420.

Computing device 400 may have additional features or functionality. For example, computing device 400 may also include additional data storage devices (removable and/or non-removable) such as, for example, magnetic disks, optical disks, or tape. Such additional storage is illustrated in FIG. 4 by a removable storage 409 and a non-removable storage 410. Computer storage media may include volatile and nonvolatile, removable and non-removable media implemented in any method or technology for storage of information, such as computer readable instructions, data structures, program modules, or other data. System memory 404, removable storage 409, and non-removable storage 410 are all computer storage media examples (i.e. memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 400. Any such computer storage media may be part of device 400. Computing device 400 may also have input device(s) 412 such as a keyboard, a mouse, a pen, a sound input device, a camera, a touch input device, etc. Output device(s) 414 such as a display, speakers, a printer, etc. may also be included. Computing device 400 may also include a vibration device capable of initiating a vibration in the device on command, such as a mechanical vibrator or a vibrating alert motor. The aforementioned devices are only examples, and other devices may be added or substituted.

Computing device 400 may also contain a network connection device 415 that may allow device 400 to communicate with other computing devices 418, such as over a network in a distributed computing environment, for example, an intranet or the Internet. Device 415 may be a wired or wireless network interface controller, a network interface card, a network interface device, a network adapter or a LAN adapter. Device 415 allows for a communication connection 416 for communicating with other computing devices 418. Communication connection 416 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both computer storage media and communication media.

As stated above, a number of program modules and data files may be stored in system memory 404, including operating system 405. While executing on processing unit 402, programming modules 406 (e.g. program module 407) may perform processes including, for example, one or more of the stages of the claimed method as described above. The aforementioned processes are examples, and processing unit 402 may perform other processes. Other programming modules that may be used in accordance with embodiments herein may include electronic mail and contacts applications, word processing applications, spreadsheet applications, database applications, slide presentation applications, drawing or computer-aided application programs, etc.

Generally, consistent with embodiments herein, program modules may include routines, programs, components, data structures, and other types of structures that may perform particular tasks or that may implement particular abstract data types. Moreover, embodiments herein may be practiced with other computer system configurations, including handheld devices, multiprocessor systems, microprocessor-based or programmable consumer electronics, minicomputers, mainframe computers, and the like. Embodiments herein may also be practiced in distributed computing environments where tasks are performed by remote processing devices that are linked through a communications network. In a distributed computing environment, program modules may be located in both local and remote memory storage devices.

Furthermore, embodiments herein may be practiced in an electrical circuit comprising discrete electronic elements, packaged or integrated electronic chips containing logic gates, a circuit utilizing a microprocessor, or on a single chip (such as a System on Chip) containing electronic elements or microprocessors. Embodiments herein may also be practiced using other technologies capable of performing logical operations such as, for example, AND, OR, and NOT, including but not limited to mechanical, optical, fluidic, and quantum technologies. In addition, embodiments herein may be practiced within a general purpose computer or in any other circuits or systems.

Embodiments herein, for example, are described above with reference to block diagrams and/or operational illustrations of methods, systems, and computer program products according to said embodiments. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments have been described, other embodiments may exist. Furthermore, although embodiments herein have been described as being associated with data stored in memory and other storage mediums, data can also be stored on or read from other types of computer-readable media, such as secondary storage devices, like hard disks, floppy disks, or a CD-ROM, or other forms of RAM or ROM. Further, the disclosed methods' stages may be modified in any manner, including by reordering stages and/or inserting or deleting stages, without departing from the claimed subject matter.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A computer implemented method for identifying and visualizing features correlated with cancer subtypes, the method comprising:

receiving a set of medical images representing an area including a patient's lesion, wherein said medical images were captured using magnetic resonance imaging (MRI), computed tomography (CT), positron emission tomography (PET), ultrasound (US), x-ray, and/or mammography, or any combination of the above;

applying a classification model trained on lesions with known pathology by mathematically combining the model's learned weights with said medical images to produce a score indicating the likelihood of the lesion being of each particular cancer subtype, wherein radiomic features are input to said classification model;

extracting importance maps from said classification model indicating features correlated with each cancer subtype by tracing the output of the model through the learned weights to identify regions of the input with a strong influence on the classification score for each cancer subtype; and displaying said importance maps as an overlay on said medical images on a computing device, wherein said overlay is color-coded to differentiate areas of importance.

2. The method of claim 1, wherein said cancer subtypes are based on clinical and biomedical knowledge, the presence or lack of specific proteins determined using immunohistochemistry assays, differential gene expression within tumors, clustering of patient case data, or any combination.

3. The method of claim 1, wherein said classification model is applied to derived images produced by pre-processing said medical images.

4. The method of claim 3, wherein said medical images are processed to remove imaging anomalies introduced by imaging equipment, reduce background noise, match signal intensities across all input images, co-register to place them within the same coordinate space, resample to the same spatial resolution, or any combination.

5. The method of claim 3, wherein said medical images are processed to segment the organ of interest.

6. The method of claim 3, wherein said medical images are processed to segment the lesion of interest.

7. The method of claim 3, wherein said medical images are processed to condense multiple images into a single image.

8. The method of claim 1, wherein said classification model is a trained convolutional neural network.

9. The method of claim 1, further comprising the use of clinical, pathology, radiology and/or genomic information as input to said classification model.

10. The method of claim 1, wherein said importance maps are generated based on class activation mapping.

11. The method of claim 1, wherein said importance maps are generated using layer-wise relevance propagation.

12. The method of claim 1, further comprising the storage of said importance map within the patient record.

13. The method of claim 1, wherein said importance maps are generated as part of a bioinformatics pipeline.

14. The method of claim 1, wherein said visualization is performed within radiological reading station software.

15. The method of claim 1, wherein said visualization is stored in PACS, exported to graphical report, and/or exported to images.

16. A computer system for identifying and visualizing features correlated with cancer subtypes, the system comprising:

a module for receiving a set of medical images representing an area including a patient's lesion, wherein said medical images were captured using magnetic resonance imaging (MRI), computed tomography (CT), positron emission tomography (PET), ultrasound (US), x-ray, and/or mammography, or any combination of the above;

a module including a classification model trained on lesions with known pathology that produces scores indicating the likelihood of the lesion belonging to each possible subtype by mathematically combining the models learned weights with said medical images, wherein radiomic features are input to said classification model;

a module including an importance map extractor that traces the output scores of said classification model through the learned weights to identify regions of said medical images with a strong influence on said output scores indicating features correlated with each cancer subtype; and a display device for displaying said importance maps as an overlay on said medical images, wherein said overlay is color-coded to differentiate areas of importance.

* * * * *